(12) United States Patent
Wang et al.

(10) Patent No.: US 12,059,421 B2
(45) Date of Patent: Aug. 13, 2024

(54) USE OF BI853520 IN CANCER TREATMENT

(71) Applicant: INXMED (NANJING) CO., LTD., Nanjing (CN)

(72) Inventors: Zaiqi Wang, Shanghai (CN); Jiangwei Zhang, Shanghai (CN); Jun Jiang, Shanghai (CN); Baoyuan Zhang, Shanghai (CN)

(73) Assignee: INXMED (NANJING) CO., LTD., Nanjing (CN)

( * ) Notice: Subject to any disclaimer, the term of this patent is extended or adjusted under 35 U.S.C. 154(b) by 0 days.

(21) Appl. No.: 18/221,588

(22) Filed: Jul. 13, 2023

(65) Prior Publication Data

US 2023/0372340 A1 Nov. 23, 2023

Related U.S. Application Data

(63) Continuation of application No. 17/780,397, filed as application No. PCT/CN2020/132244 on Nov. 27, 2020.

(30) Foreign Application Priority Data

Nov. 28, 2019 (CN) .......................... 201911191139.8
Nov. 17, 2020 (CN) .......................... 202011287049.1

(51) Int. Cl.
*A61K 31/513* (2006.01)
*A61K 31/519* (2006.01)
*A61P 35/00* (2006.01)

(52) U.S. Cl.
CPC .......... *A61K 31/513* (2013.01); *A61K 31/519* (2013.01); *A61P 35/00* (2018.01)

(58) Field of Classification Search
CPC ...... A61K 31/513; A61K 31/519; A61P 35/00
See application file for complete search history.

(56) References Cited

U.S. PATENT DOCUMENTS

| 2018/0036304 A1 | 2/2018 | Huang |
| 2018/0223377 A1 | 8/2018 | Detmer et al. |
| 2023/0000867 A1* | 1/2023 | Wang ...................... A61K 45/06 |

FOREIGN PATENT DOCUMENTS

| CN | 104478865 A | 4/2015 |
| CN | 105530937 A | 4/2016 |
| CN | 108289892 A | 7/2018 |
| EP | 4062914 A1 | 9/2022 |
| WO | 2010058032 A2 | 5/2010 |
| WO | 2017004192 A1 | 1/2017 |
| WO | 2020202005 A1 | 10/2020 |

OTHER PUBLICATIONS

Amado et al., "Wild-type KRAS is Required for Panitumumab Efficiency in Patients with Metastatic Colorectal Cancer," J Clin Oncol (2008) 26(10):1626-1634.
Baker et al., "Evaluation of Tumor Gene Expression and KRAS Mutations in FFPE Tumor Tissue as Predictors of Response to Cetuximab in Metastatic Colorectal Cancer," J Clin Oncol (2008) 26(15S): May 20 Supplement, Abstract 3512.
Doi et al., "Phase I Study of the Focal Adhesion Kinase Inhibitor BI853520 in Japanese and Taiwanese Patients with Advanced or Metastatic Solid Tumors," Targeted Oncology (2019) vol. 14, pp. 57-65.
International Search Report and Written Opinion issued in PCT/CN2020/132244 mailed Mar. 11, 2021. Chinese with English translation.
Massarelli et al., "KRAS Mutation is an Important Predictor of Resistance to Therapy with Epidermal Growth Factor Receptor Tyrosine Kinase Inhibitors in Non-Small Cell Lung Cancer," Clin Cancer Res (2007) vol. 13, No. 10, pp. 2890-2896.
Nana et al., "Role of Focal Adhesion Kinase in Small-Cell Lung Cancer and Its Potential as a Therapeutic Target," Cancers (2019) vol. 11, Article 1683, 32 pages.
Shinde et al., "Phase I study of the combination of a RAF-MEK inhibitor CH5126766 and FAK inhibitor defactinib in an intermittent dosing schedule with expansions in KRAS mutant cancers," Tumor Biology (2020) 7 pages.
Van Cutsem et al., "KRAS Status and Efficacy in the First-Line Treatment of Patients with Metastatic Colorectal Cancer (mCRC) Treated with FOLFIRI with or without Cetuximab: The CRYSTAL Experience," J Clin Oncol (2008) 26(15S): May 20 Supplement, Abstract 2.
Yoon et al., "Understanding the Roles of FAK in Cancer: Inhibitors, Genetic Models, and New Insights," Journal of Histochemistry Cytochemistry (2015) vol. 63, No. 2, pp. 114-128.
Zakowski et al., "Reflex Testing of Lung Adenocarcinomas for EGFR and KRAS Mutations: The Memorial Sloan-Kettering Experience," J bClin Oncol (2008) 26(15S): May 20 Supplement, Abstract 22031.
Hirt et al., "Efficacy of the highly selective focal adhesion kinase inhibitor BI 853520 in adenocarcinoma xenograft models is linked to a mesenchymal tumor phenotype," Oncogenesis (2018) vol. 7, Article 21, 11 pages.
Govindan et al., "Phase I study of AMG 510, a novel molecule targeting KRAS G12C mutant solid tumors," Annals of Oncology (2019) vol. 30, Supp. 5, Abstract 446PD, pp. 163-164.
Extended European Search Report issued in European Patent Application No. 20891891.2, mailed Nov. 7, 2023, 12 pages.

(Continued)

*Primary Examiner* — Erich A Leeser
(74) *Attorney, Agent, or Firm* — K&L Gates LLP

(57) ABSTRACT

The present invention relates to a method for treating a tumor with a KRAS mutation. In the method, a compound 2-fluoro-5-methoxy-4-[(4-(2-methyl-3-oxo-2,3-dihydro-1H-isoindole-4-oxy)-5-trifluoromethyl-pyrimidine-2-yl)amino]-N-(1-methyl-piperidine-4-yl)benzamide or a pharmaceutically acceptable salt thereof is administered in combination with a KRAS inhibitor or an MEK inhibitor.

15 Claims, 3 Drawing Sheets

(56) References Cited

OTHER PUBLICATIONS

Gerber et al., "Phase 2 study of the focal adhesion kinase inhibitor defactinib (VS-6063) in previously treated advanced KRAS mutant non-small cell lung cancer," Lung Cancer (2019) vol. 139, pp. 60-67.

Lee et al., "BI 853520, a FAK-Simile of Prior FAK Inhibitors?" Targeted Oncology (2019) vol. 14, No. 1, pp. 39-41.

* cited by examiner

Growth curve of MIA PaCa-2 subcutaneous xenograft tumor

USE OF BI853520 IN CANCER TREATMENT

CROSS REFERENCE TO RELATED APPLICATIONS

The present application is a continuation of U.S. application Ser. No. 17/780,397, filed May 26, 2022. U.S. application Ser. No. 17/780,397 is a national application of PCT/CN2020/132244 filed on Nov. 27, 2020, which claims the priority of the Chinese Patent Application No. 201911191139.8 filed on Nov. 28, 2019 and the Chinese Patent Application No. 202011287049.1 filed on Nov. 17, 2020. The above-identified applications are incorporated herein by reference as part of the disclosure of the present application.

FIELD OF THE INVENTION

The present disclosure belongs to the field of pharmaceutical chemistry, and particularly relates to use of a compound in the manufacture of a medicament for treating a tumor with a KRAS mutation.

BACKGROUND OF THE INVENTION

The Ras gene family encodes small GTPases involved in cell signaling. Mutations in the Ras gene can leave it permanently activated and lead to inappropriate intracellular signaling in the absence of extracellular signals. Because signaling leads to cell growth and division, dysregulated Ras signaling may ultimately lead to tumorigenesis and cancer. The Ras gene encodes the Ras superfamily proteins, which include the KRAS (Kirsten rat sarcoma viral oncogene homolog) protein encoded by the KRAS gene.

KRAS gene mutations are common in pancreatic, lung, colorectal, gallbladder, thyroid, and bile duct cancers. Epidermal growth factor receptor (EGFR) TKIs are commonly used to treat these cancers. It has been reported that KRAS mutation is a predictor of the tumor's response to epidermal growth factor receptor (EGFR) TKI targeted therapy. The most common KRAS mutations occur at codons 12 and 13 of exon 2. Other rare mutations occur at codons 59 and 61 of exon 3. Studies found that KRAS mutations at codons 12, 13 or 61 cause the Ras protein to remain in its active form for a longer time, leading to overactivation of the EGFR pathway. Therefore, patients with a KRAS mutation at codons 12, 13, or 61 do not respond well to tyrosine kinase inhibitor therapy. Furthermore, it has been shown that a KRAS mutation at codon 12 or 13 is a strong predictor of patients who are in non-response to anti-EGFR monoclonal antibody therapy such as for the treatment of certain cancerous diseases, including ERBITUX® (cetuximab; ImClone Systems Inc., New York, USA) and VECTIBIX® (panitumumab, Amgen, Thousand Oaks, CA, USA) for metastatic colorectal cancer (mCRC) and lung cancer. See Massarelli et al., KRAS Mutation is an Important Predictor of Resistance to Therapy with Epidermal Growth Factor Receptor Tyrosine Kinase Inhibitors in Non-Small Cell Lung Cancer, *CLIN CANCER RES.*, 13(10):2890-2896 (2007); Amado et al., Wild-type KRAS is Required for Panitumumab Efficiency in Patients with Metastatic Colorectal Cancer, *J. CLIN ONCOL*, 26(10):1626-1634 (2008); Van Cutsem et al., KRAS Status and Efficacy in the First-Line Treatment of Patients with Metastatic Colorectal Cancer (mCRC) Treated with FOLFIRI with or without Cetuximab: The CRYSTAL Experience, *J CLIN ONCOL*, 26(15S): May 20 Supplement, Abstract 2 (2008); Baker et al., Evaluation of Tumor Gene Expression and KRAS Mutations in FFPE Tumor Tissue as Predictors of Response to Cetuximab in Metastatic Colorectal Cancer, *J CLIN ONCOL*, 26(15S): May 20 Supplement, Abstract 3512 (2008); Van Zakowski et al., Reflex Testing of Lung Adenocarcinomas for EGFR and KRAS Mutations: The Memorial Sloan-Kettering Experience, *J. CLIN ONCOL*, 26(15S): May 20 Supplement, Abstract 22031 (2008).

Therefore, there is a need to find a therapy for cancers with a KRAS mutation.

SUMMARY OF THE INVENTION

In one aspect, the present disclosure provides use of a compound or a pharmaceutically acceptable salt thereof in the manufacture of a medicament for treating a tumor with a KRAS mutation, wherein the compound is 2-fluoro-5-methoxy-4-[(4-(2-methyl-3-oxo-2,3-dihydro-1H-isoindole-4-oxy)-5-trifluoromethyl-pyrimidine-2-yl)amino]-N-(1-methyl-piperidine-4-yl)benzamide (hereinafter referred to as "the compound", also referred to as "BI853520", see WO2010058032), wherein the compound has a structure of:

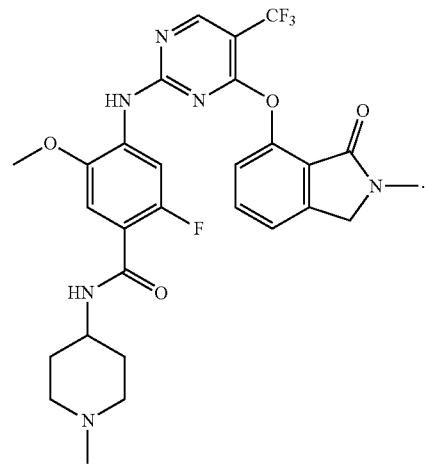

The compound was particularly effective in a tumor with a KRAS mutation (see Example 1). In addition, the compound was found to increase efficacy in combination with a KRAS inhibitor or a mitogen-activated protein kinase (MEK) inhibitor, resulting in durable and sustained tumor regression (see Examples 2 and 3).

Optionally, the tumor is pancreatic cancer, colorectal cancer, lung cancer, kidney cancer, gastric cancer, prostate cancer or ovarian cancer.

Optionally, the KRAS mutation is a G12A, G12C, G12D, G12R, G12S, G12V, G13C, G13D, G13V, Q61K, Q61L, Q61R or Q61H mutation.

Optionally, the KRAS mutation is a G12C, G12D, G13C or Q61K mutation.

Optionally, the tumor is 1) lung cancer, colorectal cancer or pancreatic cancer with a KRAS G12C mutation; 2) acute myeloid leukemia with a KRAS G12D, KRAS G12V, KRAS G13D or KRAS Q61H mutation; 3) bladder cancer with a KRAS G12C, KRAS G12D, KRAS G12R, KRAS G12V, KRAS G13D, or KRAS Q61H mutation; 4) breast cancer with a KRAS G12C, or KRAS G12V mutation; 5) cervical cancer with a KRAS G12C, KRAS G12D, KRAS G12V, or KRAS G13D mutation; 6) bile duct cancer with a KRAS G12R, or KRAS Q61K mutation; 7) colorectal cancer with a KRAS G12A, KRAS G12C, KRAS G12D, or KRAS G13D mutation; 8) esophageal cancer with a KRAS G12D mutation; 9) gastric cancer with a KRAS G12C, KRAS G12D, KRAS G12S, KRAS G12V, KRAS G13D, or KRAS Q61H mutation; 10) glioblastoma with a KRAS G12D mutation; 11) liver cancer with a KRAS G12C, KRAS G12D, or KRAS G13D mutation; 12) lung cancer with a KRAS G12A, KRAS G12D, KRAS G12S, KRAS G12V, KRAS G13C, KRAS G13D, KRAS Q61K, or KRAS Q61L mutation; 13) melanoma with a KRAS G12C, KRAS G12D, KRAS G12R, KRAS G13D, KRAS Q61K, KRAS Q61L, or KRAS Q61R mutation; 14) mesothelioma with a KRAS G12C mutation; 15) ovarian cancer with a KRAS G12R, KRAS G12V, KRAS Q61L, or KRAS G13C mutation; 16) pancreatic cancer with a KRAS G12A, KRAS G12D, KRAS G12R, KRAS G12V, KRAS G13C, or KRAS Q61H mutation; 17) prostate cancer with a KRAS G12D, KRAS G12R, or KRAS G12V mutation; 18) kidney cancer with a KRAS G12C, KRAS G12D, or KRAS G12V mutation; 19) sarcoma with a KRAS G13C, or KRAS Q61H mutation; 20) thyroid cancer with a KRAS G12V, KRAS Q61K, or KRAS Q61R mutation; 21) testicular cancer with a KRAS G12A, KRAS G12R, KRAS G12S, KRAS G12V, KRAS Q61L, or KRAS Q61R mutation; 22) thymoma with a KRAS G12D mutation; or 23) metrocarcinoma with a KRAS G12A, KRAS G12C, KRAS G12D, KRAS G12S, KRAS G12V, KRAS G13C, KRAS G13D, KRAS G13V, KRAS Q61H, or KRAS Q61L mutation.

Optionally, the pharmaceutically acceptable salt is a tartrate salt.

Optionally, the medicament is used in combination with a KRAS inhibitor, and further in combination with an effective amount of the KRAS inhibitor.

Optionally, the KRAS inhibitor is BI 1701963, JNJ-74699157, MRTX1257, MRTX849, AMG510, or a pharmaceutically acceptable salt thereof, and the AMG510 has a structure of:

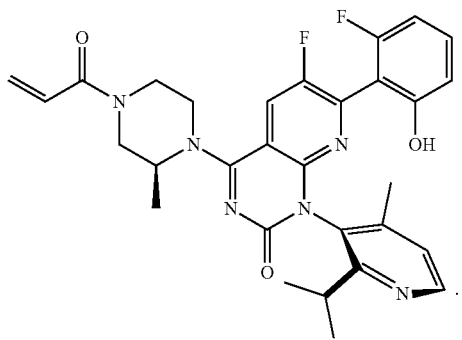

Optionally, the KRAS inhibitor is AMG510 or a pharmaceutically acceptable salt thereof.

Optionally, the tumor is lung cancer, colorectal cancer or pancreatic cancer with a KRAS mutation.

Optionally, the KRAS mutation is a G12C mutation.

Optionally, the medicament is used in combination with an MEK inhibitor, and further in combination with an effective amount of the MEK inhibitor.

Optionally, the MEK inhibitor is trametinib, cobimetinib, binimetinib, selumetinib, PD-325901, TAK-733, or a pharmaceutically acceptable salt thereof.

Optionally, the MEK inhibitor is trametinib or cobimetinib.

Optionally, the tumor is lung cancer, colorectal cancer or pancreatic cancer with a KRAS mutation.

Optionally, the KRAS mutation is a G12C mutation.

In another aspect, the present disclosure provides a method of treating a tumor with a KRAS mutation comprising administering to a subject an effective amount of a compound or a pharmaceutically acceptable salt thereof, wherein the compound has a structure of:

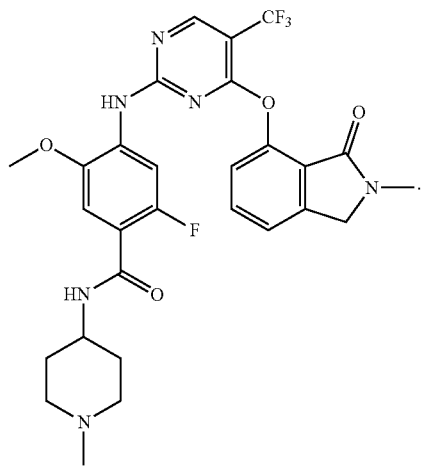

Optionally, the tumor is pancreatic cancer, colorectal cancer, lung cancer, kidney cancer, gastric cancer, prostate cancer or ovarian cancer.

Optionally, the KRAS mutation is a G12A, G12C, G12D, G12R, G12S, G12V, G13C, G13D, G13V, Q61K, Q61L, Q61R or Q61H mutation.

Optionally, the KRAS mutation is a G12C, G12D, G13C or Q61K mutation.

Optionally, the tumor is 1) lung cancer, colorectal cancer or pancreatic cancer with a KRAS G12C mutation; 2) acute myeloid leukemia with a KRAS G12D, KRAS G12V, KRAS G13D or KRAS Q61H mutation; 3) bladder cancer with a KRAS G12C, KRAS G12D, KRAS G12R, KRAS G12V, KRAS G13D, or KRAS Q61H mutation; 4) breast cancer with a KRAS G12C, or KRAS G12V mutation; 5) cervical cancer with a KRAS G12C, KRAS G12D, KRAS G12V, or KRAS G13D mutation; 6) bile duct cancer with a KRAS G12R, or KRAS Q61K mutation; 7) colorectal cancer with a KRAS G12A, KRAS G12C, KRAS G12D, or KRAS G13D mutation; 8) esophageal cancer with a KRAS G12D mutation; 9) gastric cancer with a KRAS G12C, KRAS G12D, KRAS G12S, KRAS G12V, KRAS G13D, or KRAS Q61H mutation; 10) glioblastoma with a KRAS G12D mutation; 11) liver cancer with a KRAS G12C, KRAS G12D, or KRAS G13D mutation; 12) lung cancer with a KRAS G12A, KRAS G12D, KRAS G12S, KRAS G12V, KRAS G13C, KRAS G13D, KRAS Q61K, or KRAS Q61L mutation; 13) melanoma with a KRAS G12C, KRAS G12D, KRAS G12R, KRAS G13D, KRAS Q61K, KRAS Q61L, or KRAS Q61R mutation; 14) mesothelioma with a KRAS G12C mutation; 15) ovarian cancer with a KRAS G12R, KRAS G12V, KRAS Q61L, or KRAS G13C mutation; 16) pancreatic cancer with a KRAS G12A, KRAS G12D, KRAS G12R, KRAS G12V, KRAS G13C, or KRAS Q61H mutation; 17) prostate cancer with a KRAS G12D, KRAS G12R, or KRAS G12V mutation; 18) kidney cancer with a KRAS G12C, KRAS G12D, or KRAS G12V mutation; 19) sarcoma with a KRAS G13C, or KRAS Q61H mutation; 20) thyroid cancer with a KRAS G12V, KRAS Q61K, or KRAS Q61R mutation; 21) testicular cancer with a KRAS G12A, KRAS G12R, KRAS G12S, KRAS G12V, KRAS Q61L, or KRAS Q61R mutation; 22) thymoma with a KRAS G12D mutation; or 23) metrocarcinoma with a KRAS G12A, KRAS G12C, KRAS G12D, KRAS G12S, KRAS G12V, KRAS G13C, KRAS G13D, KRAS G13V, KRAS Q61H, or KRAS Q61L mutation.

Optionally, the method further comprises administering to the subject an effective amount of a KRAS inhibitor.

Optionally, the KRAS inhibitor is BI 1701963, JNJ-74699157, MRTX1257, MRTX849, AMG510 or a pharmaceutically acceptable salt thereof, and the structure of the AMG510 is as follows:

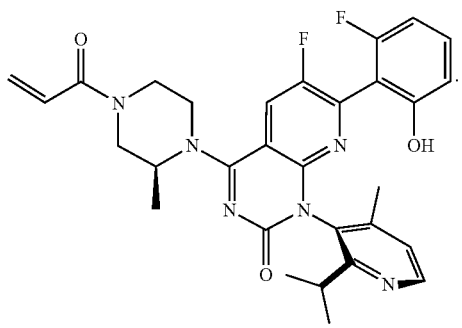

Optionally, the KRAS inhibitor is AMG510 or a pharmaceutically acceptable salt thereof.

Optionally, the tumor is lung cancer, colorectal cancer or pancreatic cancer with a KRAS mutation.

Optionally, the tumor is pancreatic cancer with a KRAS G12C mutation.

Optionally, the tumor is colorectal cancer with a KRAS G12C mutation.

Optionally, the compound or a pharmaceutically acceptable salt thereof and the KRAS inhibitor are administered simultaneously, alternately or sequentially.

Optionally, the method further comprises administering to the subject an effective amount of an MEK inhibitor.

Optionally, the MEK inhibitor is trametinib, cobimetinib, binimetinib, selumetinib, PD-325901, TAK-733, or a pharmaceutically acceptable salt thereof.

Optionally, the MEK inhibitor is trametinib or cobimetinib.

Optionally, the tumor is lung cancer, colorectal cancer or pancreatic cancer with a KRAS mutation.

Optionally, the tumor is pancreatic cancer with a KRAS G12C mutation, colorectal cancer with a KRAS G12C mutation, or lung cancer with a KRAS Q61K mutation.

Optionally, the compound or a pharmaceutically acceptable salt thereof and the KRAS inhibitor are administered simultaneously, alternately or sequentially.

Optionally, the pharmaceutically acceptable salt is a tartrate salt.

In another aspect, the present disclosure provides a method for treating a tumor with a KRAS mutation, comprising steps of:
a) assessing whether a tissue sample obtained from the subject's cancer has a KRAS mutation; and
b) administering to the subject an effective amount of the compound or a pharmaceutically acceptable salt thereof if the cancer has a KRAS mutation;

wherein the compound has a structure of:

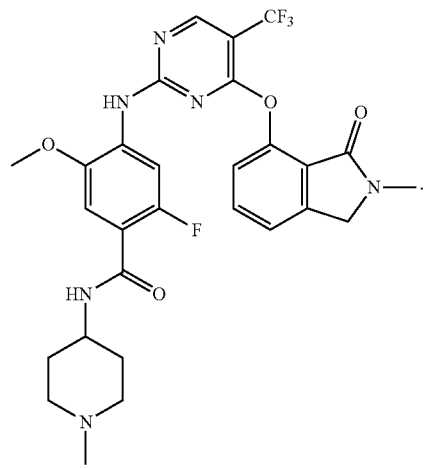

Optionally, the method further includes c) if the cancer is not characterized by a KRAS mutation, then an anticancer agent other than FAK inhibitors should be administered.

In another aspect, the present disclosure provides a pharmaceutical composition comprising a compound or a pharmaceutically acceptable salt thereof, and a KRAS inhibitor, wherein the compound has a structure of:

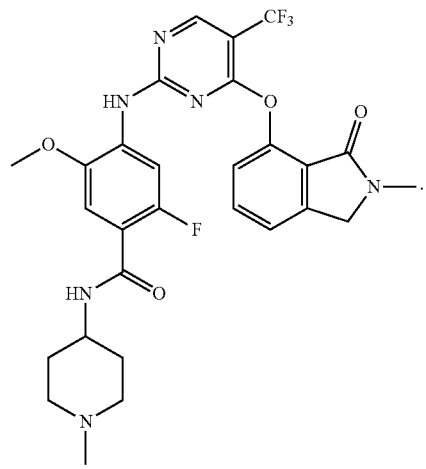

Optionally, the KRAS inhibitor is BI 1701963, MRTX849, AMG510 or a pharmaceutically acceptable salt thereof, and the AMG510 has a structure of:

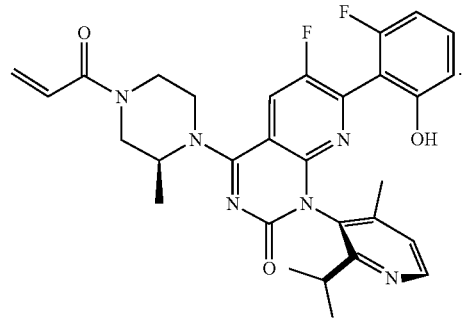

Optionally, the KRAS inhibitor is AMG510 or a pharmaceutically acceptable salt thereof.

In another aspect, the present disclosure provides a pharmaceutical composition comprising a compound or a pharmaceutically acceptable salt thereof, and an MEK inhibitor, wherein the compound has a structure of:

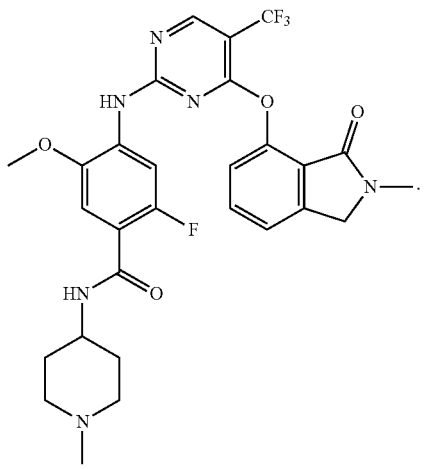

Optionally, the MEK inhibitor is trametinib, cobimetinib, binimetinib, selumetinib, PD-325901, TAK-733, or a pharmaceutically acceptable salt thereof.

Optionally, the MEK inhibitor is trametinib or a pharmaceutically acceptable salt thereof.

Optionally, the pharmaceutically acceptable salt is a tartrate salt.

In another aspect, the present disclosure provides the use of a compound or a pharmaceutically acceptable salt thereof with a KRAS inhibitor or an MEK inhibitor in the manufacture of a medicament for treating a tumor with a KRAS mutation, wherein the compound has a structure of:

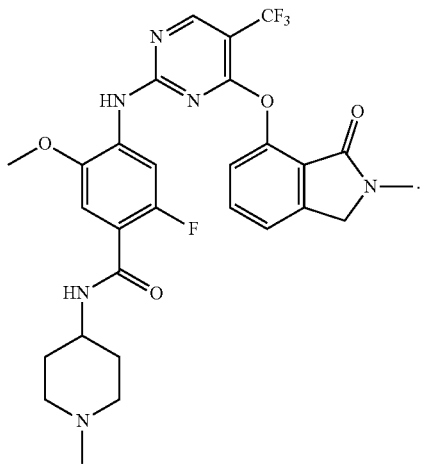

In another aspect, the present disclosure provides the use of a compound or a pharmaceutically acceptable salt thereof in the manufacture of a medicament in combination with a KRAS inhibitor or an MEK inhibitor for treating a tumor with a KRAS mutation, wherein the compound has a structure of:

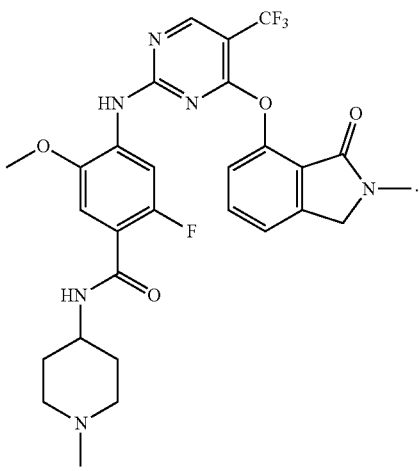

In another aspect, the present disclosure provides the use of a KRAS inhibitor or an MEK inhibitor in the manufacture of a medicament in combination with a compound or a pharmaceutically acceptable salt thereof for treating a tumor with a KRAS mutation, wherein the compound has a structure of:

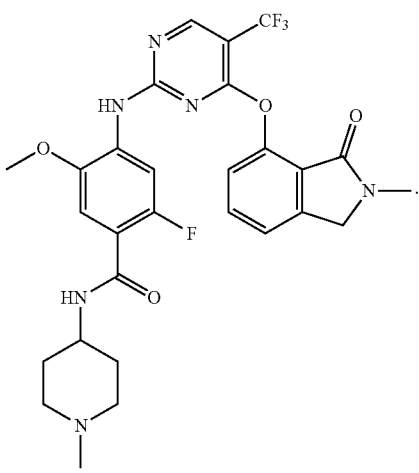

In another aspect, the present disclosure provides the following compound or a KRAS inhibitor or an MEK inhibitor or a combination thereof for use in the treatment of a tumor with a KRAS mutation, wherein the compound has a structure of:

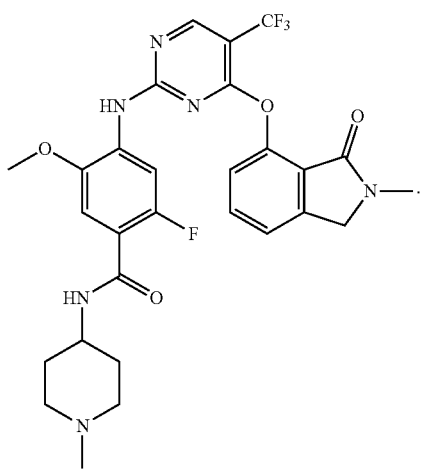

Optionally, the KRAS inhibitor or MEK inhibitor is as defined herein, and the mutation is as defined herein, and the tumor is as defined herein.

DETAILED DESCRIPTION OF THE INVENTION

Embodiments and Definitions

Figure 1:
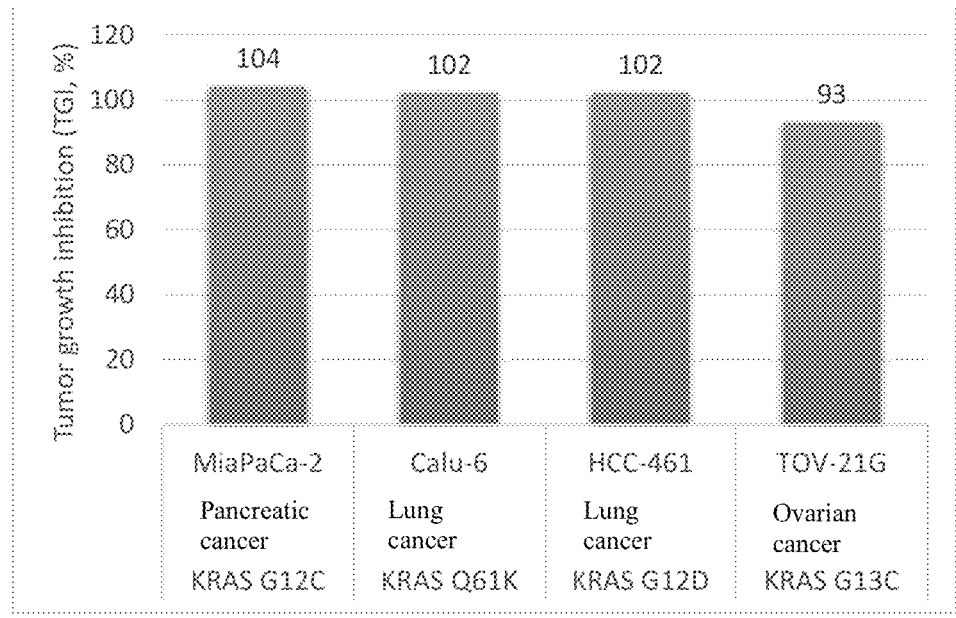
FIG. 1 depicts the anti-tumor effects of the compound, which illustrates that the compound showed tumor growth inhibition (TGI, %) at a dose of 50 mg/kg once a day in nude mouse xenograft models of human pancreatic cancer cells MIA PaCa-2 (G12C mutation), lung cancer cells Calu-6 (Q61K mutation) and HCC-461 (G12D mutation), and ovarian cancer cells TOV-21G (G13C mutation).

The present disclosure relates to the use of a compound or a pharmaceutically acceptable salt thereof in the manufacture of a medicament for treating a tumor with a KRAS mutation. The present disclosure also relates to a method of treating a tumor with a KRAS mutation comprising administering to a subject an effective amount of a compound or a pharmaceutically acceptable salt thereof.

The term "KRAS" as used herein refers to the Kirsten rat sarcoma viral oncogene homolog, a protein belonging to the RAS gene family that encodes a small G protein having intrinsic GTPase activity and contributes to the activation of downstream effectors involving multiple pathways, including apoptosis, proliferation, and differentiation.

As used herein, the term "KRAS mutation" refers to a mutation in KRAS, i.e., one or more changes in the amino acid sequence of wild-type KRAS. Mutations in KRAS can lead to loss of intrinsic GTPase activity and thus to dysregulation of cellular proliferative signaling. In some embodiments, KRAS is mutated at one or more positions selected from codons 12, 13, 59, and 61. In some embodiments, KRAS is mutated at one or more amino acid positions selected from G12, G13, S17, P34, A59, and Q61. In some embodiments, KRAS is mutated at one or more amino acid positions selected from G12C, G12S, G12R, G12F, G12L, G12N, G12A, G12D, G12V, G13C, G13S, G13D, G13V, G13P, S17G, P34S, A59E, A59G, A59T, Q61K, Q61L, Q61R, and Q61H. In some embodiments, KRAS is mutated at one or more amino acid positions selected from G12, G13, A59, Q61, K117, and A146. In some embodiments, KRAS is mutated at one or more amino acid positions selected from G12C, G12R, G12S, G12A, G12D, G12V, G13C, G13R, G13S, G13A, G13D, G13V, A59E, A59G, A59T, Q61K, Q61L, Q61R, Q61H, K117N, K117R, K117E, A146P, A146T, and A146V. In some embodiments, KRAS is mutated at one or more amino acid positions selected from G12, G13, A59, and Q61. In some embodiments, KRAS is mutated at one or more amino acid positions selected from G12C, G12R, G12S, G12A, G12D, G12V, G13C, G13R, G13S, G13A, G13D, A59E, A59G, A59T, Q61K, Q61L, Q61R, and Q61H. In some embodiments, KRAS is mutated at one or more amino acid positions selected from G12, G13, and D153. In some embodiments, KRAS is mutated at one or more amino acid positions selected from G12A, G12C, G12D, G12V, G12S, G13D, and D153V. In some embodiments, KRAS is mutated at one or more amino acid positions selected from G12C, G12S, and D153V.

In some embodiments, the KRAS mutation occurs in G12A, G12C, G12D, G12R, G12S, G12V, G13C, G13D, G13V, Q61K, Q61L, Q61R, or Q61H. In some embodiments, the KRAS mutation occurs in G12C, G12D, G13C, or Q61K.

Whether a cancer has a KRAS mutation is determined by conventional diagnostic methods for obtaining the cancer cells from a patient, including but not limited to biopsies, blood tests, and other diagnostic methods. Through these methods, samples of cancer cells, such as tissue samples, circulating tumor cells or biomolecules with characteristics of cancer (eg circulating nucleic acids) are obtained, and whether KRAS mutations are present in the cancer cells is then determined.

Methods of characterizing KRAS mutations, e.g., detection, sequencing, analysis of the KRAS gene or its expression (e.g., DNA, mRNA), include KRAS nucleic acid amplification and/or visualization. To detect the KRAS gene or its expression, nucleic acid can be isolated from a subject by conventional methods in the art, and the isolated nucleic acid can then be amplified (e.g., by polymerase chain reaction (PCR) (such as direct PCR, quantitative real-time PCR and reverse transcriptase PCR), ligase chain reaction, self-sustaining sequence replication, transcription amplification systems, Q-Beta replicase, etc.) and visualized (e.g., by labeling nucleic acids during amplification, exposure to intercalating compounds/dyes, probes). Another method for detecting KRAS mutations in codons 12 and 13 is the commercially available THERASCREEN™, a KRAS mutation test kit (DxS Limited, Manchester, UK). Additional methods for detecting KRAS mutations are disclosed in Detmer et al, US20180223377 and Huang et al., US20180036304, the entire teachings of which are incorporated herein by reference.

Another embodiment of the present disclosure is the use of the compound or a pharmaceutically acceptable salt thereof in combination with an MEK inhibitor.

The term "MEK" as used herein refers to a mitogen-activated protein kinase, a serine-threonine kinase, which mediates intracellular signaling involved in the regulation of protein and cellular functions associated with membranes, intracellular and intercellular process as well as transformation, proliferation/growth, differentiation, survival and death.

The term "MEK inhibitor" as used herein refers to a compound or agent that reduces MEK-dependent cell signaling/function, and reduces MEK-associated tumor cell proliferation/growth. Examples of MEK inhibitors include, but are not limited to, trametinib, cobimetinib, binimetinib, selumetinib, PD-325901, TAK-733, or a pharmaceutically acceptable salt thereof.

The term "KRAS inhibitor" as used herein refers to a chemical or agent that reduces KRAS activity (e.g., GTPase activity) and results in a decrease in KRAS-related apoptosis, proliferation and differentiation. Examples of KRAS inhibitors include but are not limited to BI 1701963, JNJ-74699157, MRTX1257, MRTX849, AMG510 or a pharmaceutically acceptable salt thereof. In some embodiments, examples of KRAS inhibitors include but are not limited to BI1701963, MRTX849, AMG510 or a pharmaceutically acceptable salt thereof. The BI1701963 was developed by Boehringer Ingelheim, Germany, with the US Clinical Trial Database (ClinicalTrials.gov) register number of NCT04111458. The MRTX849 was developed by the US biotechnology company Mirati, with the US Clinical Trial Database register number of NCT03785249. The AMG510 has a structure of:

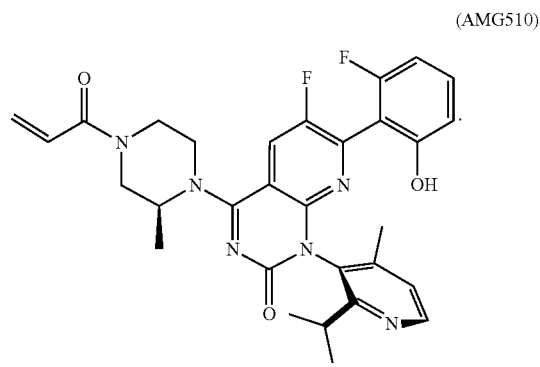

(AMG510)

The compound, or a pharmaceutically acceptable salt thereof, and the MEK inhibitor (or KRAS inhibitor) can be administered simultaneously, alternately, or sequentially.

The compound, or a pharmaceutically acceptable salts thereof, can be combined with other antiproliferative agents or anticancer therapies to treat tumors. The antiproliferative or anticancer therapy includes surgery, radiation therapy (including but not limited to gamma radiation, neutron beam radiation therapy, electron beam radiation therapy, proton therapy, brachytherapy and systemic radioisotopes), endocrine therapy, biological response modifiers (including but not limited to interferons, interleukins, and tumor necrosis factors (TNF)), hyperthermia and cryotherapy, agents to reduce any adverse effects (e.g., antiemetics), and other approved chemotherapy agents.

The compound and a pharmaceutically acceptable salts thereof can be used alone or in combination with an MEK inhibitor or a KRAS inhibitor to treat KRAS-mutant tumors. The term "KRAS-mutant tumor" as used herein refers to a tumor with a KRAS mutation. KRAS mutations result in loss of intrinsic GTPase activity and/or dysregulation of cellular proliferative signaling. In some embodiments, the tumor is selected from the group consisting of colorectal cancer, pancreatic cancer, kidney cancer, lung cancer, liver cancer, breast cancer, prostate cancer, gastrointestinal cancer, peritoneal cancer, melanoma, endometrial cancer, ovarian cancer, cervical cancer, uterine cancer, bladder cancer, glioblastoma, brain metastases, salivary gland cancer, thyroid cancer, brain cancer, lymphoma, myeloma and head and neck cancer. In some embodiments, the tumor is selected from squamous cell carcinoma, small cell lung cancer, non-small cell lung cancer, lung adenocarcinoma, lung squamous carcinoma, hepatocellular carcinoma, colon cancer, endometrial cancer, and hepatocellular carcinoma. In some embodiments, the tumor is selected from the group consisting of colorectal cancer, prostate cancer, breast cancer, lung cancer, endometrial cancer, multiple myeloma, pancreatic cancer, renal cancer, and glioblastoma. In some embodiments, the tumor is selected from non-small cell lung cancer, pancreatic cancer, and glioblastoma. In some embodiments, the tumor is non-small cell lung cancer. In some embodiments, the KRAS-mutant tumor is pancreatic cancer, colorectal cancer, lung cancer, kidney cancer, gastric cancer, prostate cancer, ovarian cancer, breast cancer, brain cancer, bladder cancer, cervical cancer, esophageal cancer, liver cancer, thyroid cancer, testicular cancer, uterine cancer, thymoma, hepatocellular carcinoma, head and neck cancer, bile duct cancer, neuroblastoma, melanoma, glioblastoma, lymphoma, leukemia, acute myeloid leukemia, melanoma, mesothelioma, sarcoma, paraganglioma, osteosarcoma, germ cell tumor, or mesothelioma. In some embodiments, the KRAS-mutant tumor is pancreatic cancer, colorectal cancer, lung cancer, kidney cancer, gastric cancer, prostate cancer, or ovarian cancer.

In some embodiments, specific examples of the KRAS-mutant tumor include 1) lung cancer, colorectal cancer or pancreatic cancer with a KRAS G12C mutation; 2) acute myeloid leukemia with a KRAS G12D, KRAS G12V, KRAS G13D or KRAS Q61H mutation; 3) bladder cancer with a KRAS G12C, KRAS G12D, KRAS G12R, KRAS G12V, KRAS G13D, or KRAS Q61H mutation; 4) breast cancer with a KRAS G12C, or KRAS G12V mutation; 5) cervical cancer with a KRAS G12C, KRAS G12D, KRAS G12V, or KRAS G13D mutation; 6) bile duct cancer with a KRAS G12R, or KRAS Q61K mutation; 7) colorectal cancer with a KRAS G12A, KRAS G12C, KRAS G12D, or KRAS G13D mutation; 8) esophageal cancer with a KRAS G12D mutation; 9) gastric cancer with a KRAS G12C, KRAS G12D, KRAS G12S, KRAS G12V, KRAS G13D, or KRAS Q61H mutation; 10) glioblastoma with a KRAS G12D mutation; 11) liver cancer with a KRAS G12C, KRAS G12D, or KRAS G13D mutation; 12) lung cancer with a KRAS G12A, KRAS G12D, KRAS G12S, KRAS G12V, KRAS G13C, KRAS G13D, KRAS Q61K, or KRAS Q61L mutation; 13) melanoma with a KRAS G12C, KRAS G12D, KRAS G12R, KRAS G13D, KRAS Q61K, KRAS Q61L, or KRAS Q61R mutation; 14) mesothelioma with a KRAS G12C mutation; 15) ovarian cancer with a KRAS G12R, KRAS G12V, KRAS Q61L, or KRAS G13C mutation; 16) pancreatic cancer with a KRAS G12A, KRAS G12D, KRAS G12R, KRAS G12V, KRAS G13C, or KRAS Q61H mutation; 17) prostate cancer with a KRAS G12D, KRAS G12R, or KRAS G12V mutation; 18) kidney cancer with a KRAS G12C, KRAS G12D, or KRAS G12V mutation; 19) sarcoma with a KRAS G13C, or KRAS Q61H mutation; 20) thyroid cancer with a KRAS G12V, KRAS Q61K, or KRAS Q61R mutation; 21) testicular cancer with a KRAS G12A, KRAS G12R, KRAS G12S, KRAS G12V, KRAS Q61L, or KRAS Q61R mutation; 22) thymoma with a KRAS G12D mutation; or 23) metrocarcinoma with a KRAS G12A, KRAS G12C, KRAS G12D, KRAS G12S, KRAS G12V, KRAS G13C, KRAS G13D, KRAS G13V, KRAS Q61H, or KRAS Q61L mutation.

In some embodiments, the compound or a pharmaceutically acceptable salt thereof of the present disclosure is used in combination with an MEK inhibitor (e.g., trametinib, cobimetinib, binimetinib, selumetinib, PD-325901, TAK-733, especially trametinib) for the treatment of KRAS-mutant lung, colorectal or pancreatic cancer. The KRAS mutation can be any one of the above-mentioned mutations. In one embodiment, the KRAS mutation is a G12C mutation.

In some embodiments, the compound, or a pharmaceutically acceptable salt thereof, is used in combination with a KRAS inhibitor (e.g., BI 1701963, MRTX849, and AMG510, especially AMG510) for the treatment of KRAS-mutant lung, colorectal, or pancreatic cancer. The KRAS mutation can be any one of the above-mentioned mutations. In one embodiment, the KRAS mutation is a G12C mutation.

As used herein, the term "pharmaceutically acceptable" means non-toxic, biologically tolerable and suitable for administration to a subject.

As used herein, the term "pharmaceutically acceptable salt" refers to a salt that is non-toxic, biologically tolerable and suitable for administration to a subject. The pharmaceutically acceptable salts of the compounds refer to an acid addition salt that is non-toxic, biologically tolerable and suitable for administration to a subject, including but not limited to: acid addition salts formed by the compounds with an inorganic acid, such as hydrochloride, hydrobromide, carbonate, bicarbonate, phosphate, sulfate, sulfite, nitrate, and the like, as well as acid addition salts formed by the compounds with an organic acid, such as formate, acetate, malate, maleate, fumarate, tartrate, succinate, citrate, lactate, methanesulfonate, p-toluenesulfonate, 2-hydroxyethanesulfonate, benzoate, salicylate, stearate, and salts formed with alkane-dicarboxylic acid of formula HOOC—$(CH_2)_n$—COOH (wherein n is 0-4), etc. Pharmaceutically acceptable salts can be obtained by conventional methods well known in the art, for example by reacting a sufficiently basic compound such as an amine with a suitable acid which provides a physiologically acceptable anion. In some embodiments, the salt is a tartrate salt.

As used herein, the term "subject" refers to mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

The term "treat", "treating" or "treatment" as used herein refers to obtaining a desired pharmacological and/or physiological effect. The effect may be therapeutic and includes partial or substantial achievement of one or more of the following: partial or total reduction in the extent of the disease, condition or syndrome; improvement in clinical symptoms or indicators associated with the disease; or delaying, inhibiting or reducing likelihood of progression of the disease, condition or syndrome.

The term "effective amount" as used herein refers to an amount of the compound (or a pharmaceutically acceptable salt thereof), an MEK inhibitor and/or a KRAS inhibitor sufficient to reduce or ameliorate the severity, duration, progression, or onset of the disease or condition, to delay or arrest the progression of the disease or condition, to cause regression of the disease or condition or delay the recurrence or progression of symptoms, or to enhance or improve the therapeutic effect of another therapy. The precise amount of the compound (or a pharmaceutically acceptable salt thereof), MEK inhibitor and/or KRAS inhibitor administered to a subject will depend on various factors, such as the given agent or compound, pharmaceutic preparation, route of administration, the type of disease, the condition, the identity of the subject or host being treated, etc., but can still be routinely determined by those skilled in the art. For example, determination of an effective amount will also depend on the degree, severity, and type of cell proliferation. The skilled artisan will be able to determine the appropriate dosage based on these and other factors. When co-administered with other therapeutic agents, e.g., when co-administered with an anticancer agent, the "effective amount" of any other therapeutic agent will depend on the type of the agent used. Appropriate dosages are known for approved therapeutics and can be adjusted by the skilled artisan depending on the condition of the subject, the type of condition being treated, and the amount of the compound or a pharmaceutically acceptable salt thereof. In cases where the amount is not explicitly stated, the amount should be assumed to be an effective amount. An effective dose of the compound or a pharmaceutically acceptable salt thereof may range from 10 µg to 2000 mg. This example is non-limiting. Effective amounts of MEK inhibitors and KRAS inhibitors are known to those skilled in the art.

The compounds or pharmaceutically acceptable salts thereof can be administered by any suitable method of administration. Suitable methods include oral, enteral, parenteral, intravenous, intramuscular or subcutaneous administration to the subject.

Thus, the compound or a pharmaceutically acceptable salt thereof can be administered orally with a pharmaceutically acceptable carrier such as an inert diluent or an absorbable edible carrier. They can be enclosed in hard- or soft-shell gelatin capsules, compressed into tablets, or mixed directly with the patient's food. For oral therapeutic administration, the compound, or a pharmaceutically acceptable salt thereof, can be combined with one or more excipients and used in a form of ingestible tablets, buccal tablets, lozenges, capsules, elixirs, suspensions, syrups or wafers. These preparations contain an effective amount of the compound.

Tablets, lozenges, pills, capsules, etc. may further comprise: binders such as tragacanth, acacia, cornstarch or gelatin; excipients such as dicalcium phosphate; disintegrants such as corn starch, potato starch, alginic acid, etc.; lubricants, such as magnesium stearate; or sweeteners, such as sucrose, fructose, lactose or aspartame; or flavoring agents.

The compounds may also be administered intravenously or intraperitoneally by infusion or injection. Solutions of the compounds can be prepared in water, optionally mixed with nontoxic surfactants.

Exemplary pharmaceutical dosage forms for injection or infusion include: sterile aqueous solutions, dispersions, or sterile powders containing the active ingredient suitable for the extemporaneous preparation of sterile injectable or infusion solutions or dispersions. In any event, the final dosage form should be sterile, fluid, and stable under the conditions of manufacture and storage.

Sterile injectable solutions can be prepared by incorporating a required amount of the compound in an appropriate solvent together with other desired ingredients enumerated above and then being filtrated and sterilized. In the case of sterile powders for preparing sterile injectable solutions, the preferred methods of preparation may be vacuum drying and the freeze-drying techniques, which yield a powder of the active ingredient plus any other desired ingredients previously present after sterile filtration.

The amount of compound required for treatment may vary not only with the particular salt chosen, but also with the route of administration, the nature of the disease being treated, and the age and condition of the patient, and is ultimately at the discretion of the attending physician or clinician. However, the dosage may generally range from about 0.1 to about 50 mg/kg body weight per day.

The desired dose may conveniently be presented as a single dose or as divided doses for administration at appropriate intervals.

The term "FAK inhibitor" as used herein refers to a potent inhibitor of FAK, which may be suitable for mammals, particularly humans.

EXAMPLES

The following examples are provided to further illustrate the present disclosure. It should be understood that these examples are only used to illustrate the present disclosure and not to limit the scope of the present disclosure.

The experimental methods without specific conditions in the following examples can be carried out according to the conventional conditions of this type of reaction or according to the conditions suggested by the manufacturer.

The experimental materials and reagents used in the following examples can be obtained from commercial sources unless otherwise specified.

The meanings of the abbreviations used in the examples are as follows:
ATCC American Type Culture Collection
$CO_2$ Carbon dioxide
d Days
FCS Fetal Calf Serum
kg Kilograms
l Liter
mg Milligram
ml Milliliter
$mm^3$ Cubic millimeter
PBS Phosphate Buffered Saline
RPMI 1640 RPMI 1640 Medium
p.o. Oral
qd/QD Daily
TGI Tumor Growth Inhibition Generic Xenograft Models for Antitumor Study:

The study used a nude mouse xenograft model of human cancer cells with KRAS mutations. Athymic Female BomTac: approximately 6-week-old NMRI-Foxn1nu mice were purchased from Taconic®, Denmark. After arriving in the animal room, mice were acclimated to the new environment for at least 3 days before being used for assay. The animals were housed under standard conditions (temperature 21.5±1.5° C. and 55±10% humidity) with 5 mice in each group. The animals were provided standard diet and autoclaved tap water ad libitum. A Datamars® T-IS 8010 FDX-B transponder implanted subcutaneously in the neck region and a LabMax® II fixed reader were used to identify each mouse. The cage card showing the study number, animal identification number, compound and dose level, route of administration, and dosing schedule for the animal throughout the assay was retained on the animals.

To establish subcutaneous tumors, Human cancer cells having a KRAS mutation were harvested by trypsinization, centrifuged, washed and suspended in ice-cold PBS+5% FCS and growth factor reduced Matrigel (1:1) at a cell concentration of $1\times10^8$ cells/ml. Then 100 µl of cell suspension containing $2.5\times10^6$-$1\times10^7$ cells was injected subcutaneously into the right flank of nude mice (1 site per mouse). When tumors were established and reached a diameter of 6-8 mm (7 days after cell injection), mice were randomly assigned to the treatment group and the control group.

Compounds suspended in 1M HCl and diluted with 0.5% hydroxyethyl cellulose were administered intragastrically through gavage needle every day, and the dosage was 10 mL/Kg.

Tumor diameters were measured with calipers three times a week (Monday, Wednesday, and Friday). The volume of each tumor [in $mm^3$] was calculated according to the equation, "tumor volume=length×$diameter^2$×π/6". To monitor the side effects of the treatment, the mice were checked daily for abnormalities and their body weights were measured three times a week (Monday, Wednesday, and Friday). Animals were sacrificed at the end of the study (approximately three weeks after the start of treatment). During the study animals with tumor necrosis or tumors larger than 2000 mm$^3$ were sacrificed ahead of schedule for ethical reasons.

At the end of the assay, statistical evaluation of tumor volume and body weight parameters was performed. Absolute tumor volume and percent change in body weight (referenced to initial weight on day 1) were used. A non-parametric approach was used, and the number of observations, median, minimum and maximum values were calculated. For a quick overview of possible treatment effects, the median tumor volume for each treatment group T and the median tumor volume for the control group C were used to calculate the TGI from day 1 to day d:

Relative tumor volume: (T/C)

$$T/C = 100 * \frac{T_d}{C_d}$$

TGI from day 1 to day d:

$$TGI = 100 * \frac{(C_d - C_1) - (T_d - T_1)}{(C_d - C_1)}$$

wherein,
$C_1$, $T_1$=median tumor volume in control and treatment groups at the start of the assay (day 1).
$C_d$, $T_d$=median tumor volume in control and treatment groups at the end of the assay (day d).

Each dose of test compound was compared to the control group using a one-sided descending wilcoxon test, taking reduction in tumor volume as a treatment effect and weight loss as a side effect. The P-values for tumor volume (the efficacy parameter) were compared and adjusted for multiple times according to Bonferroni-Holm, while the P-values for body weight (the tolerance parameter) were not adjusted so as not to overlook possible side effects. Significance level was fixed at α=5%. A p-value (adjusted) of less than 0.05 was considered to show a statistically significant difference between groups, and 0.05≤p-value<0.10 was considered as an indicative difference. Statistical evaluations were performed using the software packages SAS version 9.2 (SAS Institute Inc., Cary, NC, USA) and Proc StatXact® version 8.0 (Cytel Software, Cambridge, MA, USA).

Example 1: Antitumor Activity Study of the Compound in Xenograft Models

This study followed the procedure described in Generic Xenograft Models for Antitumor Study.

The cell lines used in this assay were obtained from ATCC, including pancreatic cancer cells MIA PaCa-2 (G12C mutation), lung cancer cells Calu-6 (Q61K mutation) and HCC-461 (G12D mutation), and ovarian cancer cells TOV-21G (G13C mutation) (FIG. 1). A master cell bank and a working cell bank (WCB) were established according to BI RCV GmbH & Co KG standards. Cells were grown in T175 tissue culture flasks using the following media:
  MIA PaCa-2: DMEM+GlutaMax, supplemented with 10% heat-inactivated fetal bovine serum, 1% non-essential amino acids and 1% sodium pyruvate;
  TOV-21G: MCDB 105 medium containing 1.5 g/L sodium bicarbonate was mixed with medium 199 containing 15% heat-inactivated FCS at a ratio of 1:1;
  Calu-6: MEM+1% NEAA+1% sodium pyruvate+1% GlutaMax+10% FCS;
  HCC-461: RPMI-1640/GlutaMAX, 10% FCS.

Cells were cultured in humidified air at 37° C. and 5% $CO_2$. Cultures were maintained at a concentration of 8×10$^6$ cells/ml to 12×10$^7$ cells/ml. The number of inoculations of each cell to establish a tumor model was as follows: MIA PaCa-2 (1×10$^7$), TOV-21G (5×10$^6$), Calu-6 (2.5×10$^6$), and HCC-461 (5×10$^6$).

Five independent tests were performed. In each test, ten or twelve tumor-bearing mice in each group were treated with either the control formulation or the compound, respectively. Treatment was initiated when the median tumor volume reached approximately 50-100 mm$^3$ and terminated after 2 to 4 weeks. The compound in the treatment group was suspended in 0.5% hydroxyethyl cellulose and administered daily at a dose of 50 mg/kg, while the control group was treated with 0.5% hydroxyethyl cellulose alone.

After treatment with 50 mg/kg of the compound once a day, the TGI of pancreatic cancer cells MIA PaCa-2, lung cancer cells Calu-6 and HCC-461, and ovarian cancer cells TOV-21G ranged from 93% to 104% (p<0.0001) (FIG. 1).

Example 2: Antitumor Study of the Compound and KRAS Inhibitors in the MIA PaCa-2 Cell Line Xenograft Model This study followed the procedure described in Generic Xenograft Models for Antitumor Study.

Human pancreatic cancer MIA PaCa-2 cells harboring the KRAS G12C mutation were obtained from ATCC. A master cell bank (MCB) and a working cell bank (WCB) were established according to BI RCV GmbH & Co KG standards. Cells used in each assay were obtained from WCB 16.10.2006 (Lab Tontsch-Grunt) or WCB 11.02.2009 (Lab Hirt). Cells were grown in T175 tissue culture flasks containing DMEM+GlutaMax supplemented with 10% heat-inactivated fetal bovine serum, 1% non-essential amino acids and 1% sodium pyruvate. Cells were cultured in humidified air at 37° C. and 5% $CO_2$. Cultures were maintained at a concentration of 1×10$^6$ cells/ml to 3×10$^6$ cells/ml.

Each group of 4 tumor-bearing mice was treated as follows: the control group (treated with 0.5% hydroxyethyl cellulose), the compound group (suspended in 0.5% hydroxyethyl cellulose, administered daily at a dose of 25 mg/kg), the AMG510 (KRAS inhibitor) group (suspended in 0.5% hydroxyethyl cellulose, administered daily at a dose of 10 mg/kg), and the combination group of the compound (suspended in 0.5% hydroxyethyl cellulose, administered daily at a dose of 25 mg/kg) and AMG510 (suspended in 0.5% hydroxyethyl cellulose, administered daily at a dose of 10 mg/kg). The treatment was initiated when the median volume of the tumor reached about 200 mm$^3$. After 11 days of continuous administration, the administration was stopped on the 12th day, and the tumor growth of the mice was continued to be observed.

Figure 2:
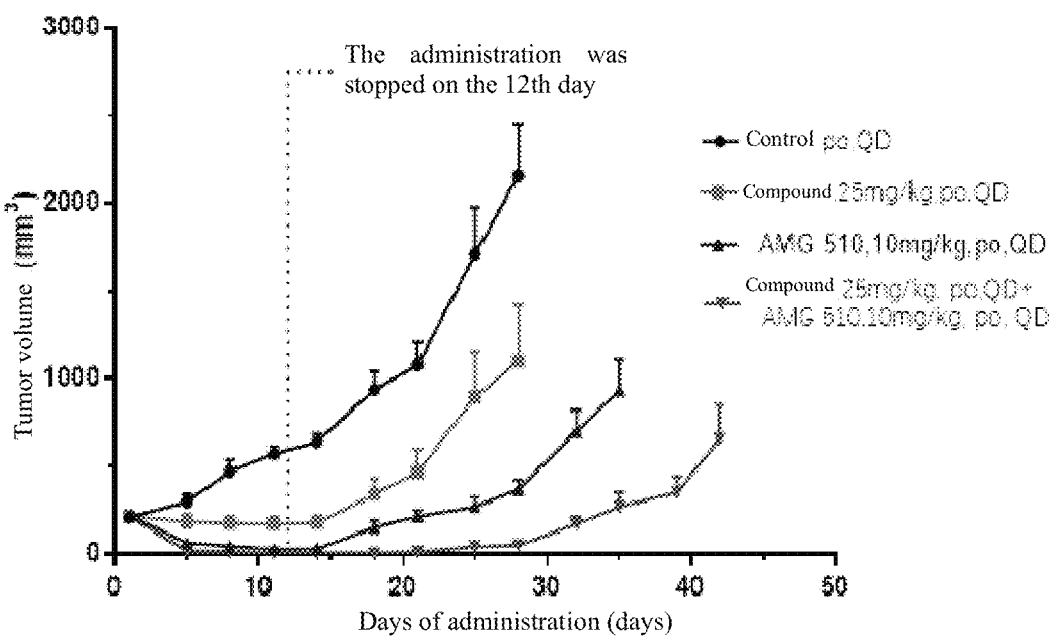
FIG. 2 depicts the tumor growth kinetics of the nude mouse xenograft model of pancreatic cancer cell MIA PaCa-2, which illustrates the antitumor effects of different test groups in the nude mouse xenograft model of pancreatic cancer cell MIA PaCa-2 (Example 2). The test groups were the control group; the compound group, administered once a day with a dose of 25 mg/kg; the AMG510 group, administered once a day with a dose of 10 mg/kg; the combined administration group of the compound and AMG510, with the compound administered once a day at a dose of 25 mg/kg and AMG510 administered once a day at a dose of 10 mg/kg; respectively.
Figures 3, 4:
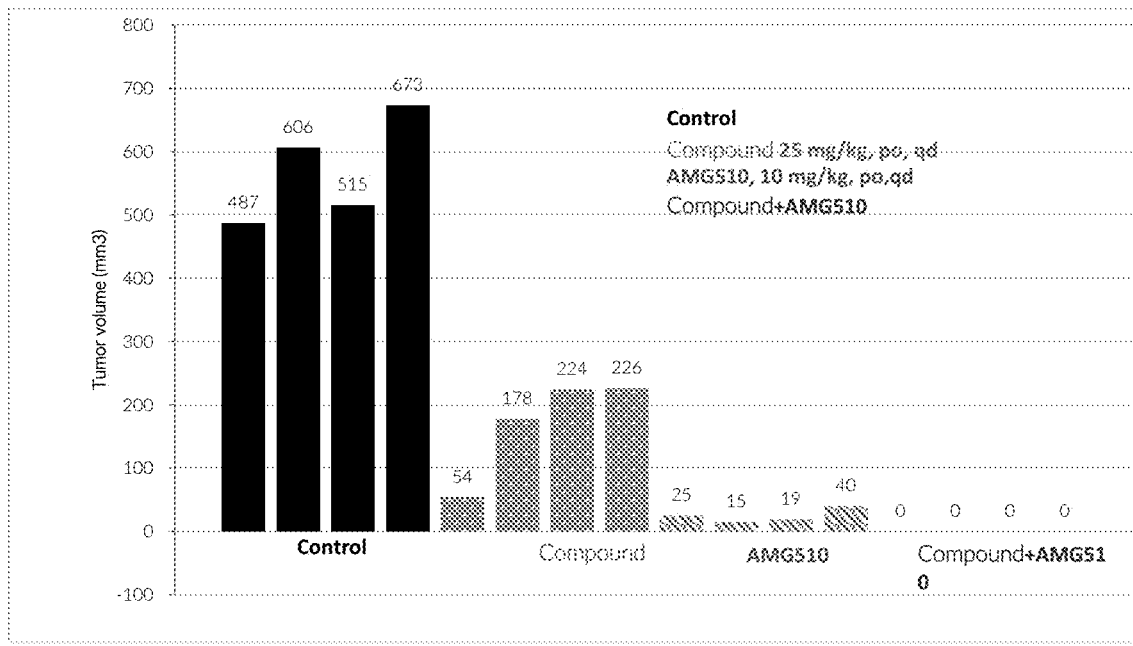
FIG. 3 depicts the tumor volume (mm$^3$) of animals in the nude mouse xenograft model of pancreatic cancer cell MIA PaCa-2 at day 11, which illustrates the antitumor effects of different test groups in the nude mouse xenograft model of pancreatic cancer cell MIA PaCa-2 (Example 2). The test groups were the control group; the compound group, administered once a day with a dose of 25 mg/kg; the AMG510 group, administered once a day with a dose of 10 mg/kg; the combined administration group of the compound and AMG510, with the compound administered once a day at a dose of 25 mg/kg and AMG510 administered once a day at a dose of 10 mg/kg; respectively.
FIG. 4 depicts the mean tumor volume (mm$^3$) of the nude mouse xenograft model of lung cancer cell Calu-6, which illustrates the antitumor effect of different test groups in the nude mouse xenograft model of lung cancer cell Calu-6 (Example 3). The test groups were the control group; the compound group, administered once a day with a dose of 50 mg/kg; the trametinib group, administered once a day with a dose of 0.125 mg/kg; the combined administration group of the compound and trametinib, with the compound administered once a day at a dose of 50 mg/kg and trametinib administered once a day at a dose of 0.125 mg/kg; respectively.

100% of tumors disappeared in the combination group of the compound at 25 mg/kg and AMG510 at 10 mg/kg (FIG. 2 and FIG. 3).

In the MIA PaCa-2 cell model of pancreatic cancer with a KRAS G12C mutation, combination of the compound and the KRAS inhibitor showed good synergistic effect.

Example 3: Antitumor Study of the Compound and MEK Inhibitors in the Calu-6 Cell Line Xenograft Model This study followed the procedure described in Generic Xenograft Models for Antitumor Study.

Human lung cancer Calu-6 cells harboring the KRAS Q61K mutation were obtained from ATCC. A master cell bank (MCB) and a working cell bank (WCB) were established according to BI RCV GmbH & Co KG standards. Cells used in each assay were obtained from WCB 16.10.2006 (Lab Tontsch-Grunt) or WCB 11.02.2009 (Lab Hirt). Cells were grown in T175 tissue culture flasks containing MEM+1% NEAA+1% sodium pyruvate+1% Gluta-Max+10% FCS as medium. Cells were cultured in humidified air at 37° C. and 5% $CO_2$. Cultures were maintained at a concentration of $2.5 \times 10^6$ cells/ml.

Each group of 10 tumor-bearing mice was treated as follows: the control group (treated with 0.5% hydroxyethyl cellulose), the compound group (suspended in 0.5% hydroxyethyl cellulose, administered daily at a dose of 50 mg/kg), the trametinib (MEK inhibitor) group (suspended in 0.5% hydroxyethyl cellulose, administered daily at a dose of 0.125 mg/kg), and the combination group of the compound (suspended in 0.5% hydroxyethyl cellulose, administered daily at 50 mg/kg) and AMG510 (suspended in 0.5% hydroxyethyl cellulose, administered daily at a dose of 0.125 mg/kg). Treatment was initiated when the median tumor volume reached approximately 200 mm³ and terminated when the tumor volume exceeded 1000 mm³.

Tumor volume was significantly reduced in the combination group of the compound at 50 mg/kg and trametinib at 0.125 mg/kg (FIG. 4).

In the Calu-6 cell model of lung cancer with a KRAS Q61K mutation, combination of the compound and the MEK inhibitor showed good synergistic effect.

Example 4: Antitumor Study of the Compound and KRAS Inhibitors in the CO-04-0070 (KRAS G12C Mutation) Subcutaneous Xenograft Model 6- to 8-week-old BALB/c nude mice were purchased from Beijing Vital River Laboratory Animal Technology Co., Ltd. After arriving in the animal room, mice were acclimated to the new environment for at least 3 days before being used for the assay. The animals were housed under standard conditions (temperature 20-26° C. and 40-70% humidity) with 5 animals per group. The animal information card for each cage indicated the quantity, sex, strain, date of receipt, dosing schedule, experiment number, group, and the start date of the assay for the animals in the cage. All cages, litter and drinking water were sterilized prior to use. Cages, feed and drinking water were changed twice a week. Animals in the assay were identified by ear tags.

The human-derived colorectal cancer CO-04-0070 model was originally derived from tumor samples resected during clinical surgery. After the surgically resected tumor specimens were sequenced for mutation and gene expression using next-generation sequencing technology, the tumor tissue was cut into 20-30 mm³, and then inoculated into several mice. Tumor tissue that can grow smoothly would be excised and cryopreserved in liquid nitrogen for subsequent resuscitation.

The nomenclature of passage was that nude mice inoculated with tumor samples was P0 generation, which continued to passage as P1 generation, and so on, and the resuscitated specimen was named as FP. The tumor tissue used in this assay was the FP3 generation. A 20-30 mm³ of CO-04-0070 FP3 tumor tissue mass was subcutaneously inoculated into the right back of each mouse, and tumor growth was awaited. Randomization was performed for groups when the mean tumor volume reached about 112 mm³ (Table 1).

TABLE 1

Animal grouping and dosing schedule

| Group | N[1] | Compound therapy | Dosage (mg/kg) | Dosing volume parameters (µL/g)[2] | Route of administration | Dosing frequency |
|---|---|---|---|---|---|---|
| 1 | 4 | Control | — | 10 | PO | QD × 22 |
| 2 | 4 | The compound | 25 | 10 | PO | QD × 22 |
| 3 | 5 | AMG510 | 30 | 10 | PO | QD × 33 |
| 4 | 5 | The compound + AMG510 | 25 + 30 | 10 | PO | QD × 33 |

Note:
[1]N: The quantity of mice in each group;

Tumor-bearing mice in each group were treated as follows: the control group (treated with 0.5% hydroxyethyl cellulose), the AMG510 (KRAS inhibitor) group (suspended in 0.5% hydroxyethyl cellulose, administered daily at a dose of 30 mg/kg), and the combination group of the compound (suspended in 0.5% hydroxyethyl cellulose, administered daily at a dose of 25 mg/kg) and AMG510 (suspended in 0.5% hydroxyethyl cellulose, administered daily at a dose of 30 mg/kg).

The indicator of the assay was to examine whether tumor growth was inhibited, delayed or cured. Tumor diameters were measured with vernier calipers twice a week. The equation for calculating tumor volume was: $V = 0.5a \times b^2$, wherein a and b represented the long and short diameters of the tumor, respectively.

The antitumor efficacy of the compounds was evaluated by TGI (%) or tumor proliferation rate T/C (%).

TGI (%), reflecting tumor growth inhibition rate, was calculated:

TGI (%)=[1−(mean tumor volume at the end of administration in a certain treatment group−mean tumor volume at the beginning of administration in this treatment group)/(mean tumor volume at the end of treatment in the control group−mean tumor volume at the beginning of treatment in the control group)]×100%.

Tumor proliferation rate T/C (%) was calculated as follows:

$T/C\ (\%) = Ti/Vi \times 100$.

Wherein, Vi is the mean tumor volume of the solvent control group in a certain measurement, and Ti is the mean tumor volume of the administration group in the same measurement.

After the assay, the tumor weights were detected, and the percentages of $T/C_{weight}$ were calculated. $T_{weight}$ and $C_{weight}$ represented the tumor weight of the administration group and the solvent control group, respectively.

Statistical analysis includes mean and standard error of mean (SEM) of tumor volume at each time point for each group. Statistical analysis was performed to evaluate the differences between groups based on the data on the 21st day after the start of administration, and one-way ANOVA was used to analyze the comparison between multiple groups. Because of the significant difference in F value, the Games-Howell method was used for test. All data analyses were performed with SPSS 17.0, and $p < 0.05$ was considered as a significant difference.

Figure 5:
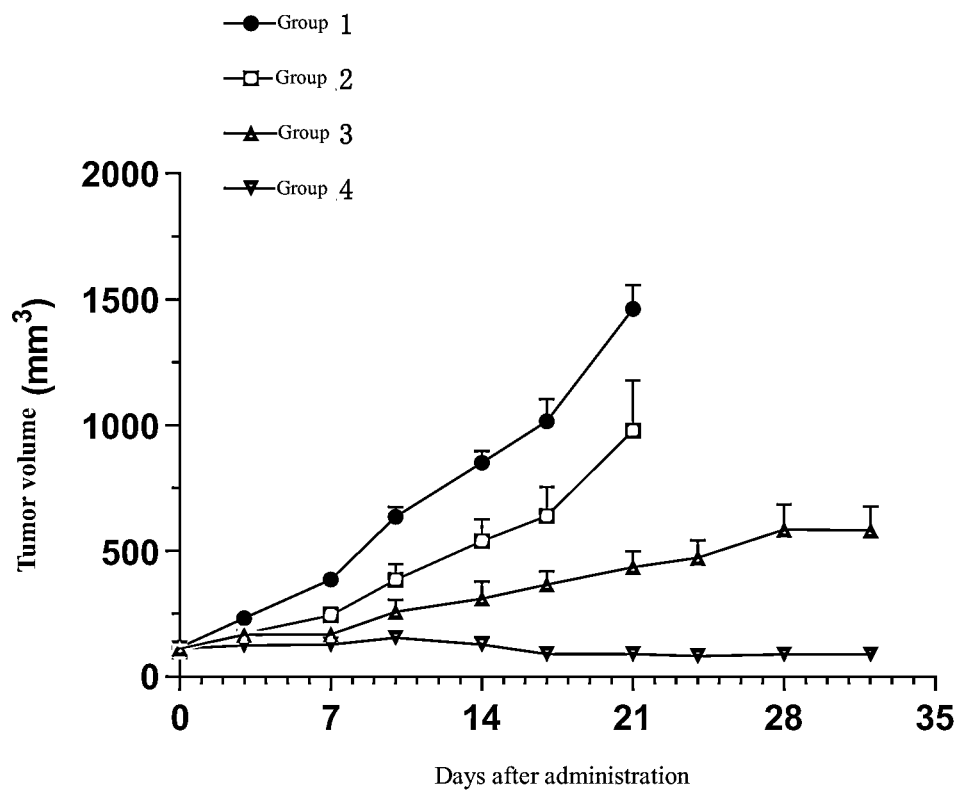
FIG. 5 depicts the tumor growth kinetics of the nude mouse patient derived xenograft model of colorectal cancer CO-04-0070, which illustrates the antitumor effects of different test groups in the nude mouse xenograft model of colorectal cancer CO-04-0070 (Example 4). The test groups were the control group; the compound group, administered once a day with a dose of 25 mg/kg; the AMG510 group, administered once a day with a dose of 30 mg/kg; the combined administration group of the compound and AMG510, with the compound administered once a day at a dose of 25 mg/kg and AMG510 administered once a day at a dose of 30 mg/kg; respectively.

Results of Assay:

On the 21st day after the start of administration, the tumor volume of the tumor-bearing mice in the control group reached 1,388 mm³. Compared with the control group, the tumor volume of animals in group 2, group 3 and group 4 was 978 mm³ (T/C=66.89%, TGI=35.34%, p=0.04), 436 mm³ (T/C=31.38%, TGI=74.63%, p=0.001), and 91 mm³ (T/C=6.57%, TGI=101.65%, p=0.001), respectively, all of which had tumor-suppressive effects (FIG. 5).

In the CO-04-0070 model of colorectal cancer with a KRAS G12C mutation, combination of the compound and the KRAS inhibitor AMG510 showed good synergistic effect.

The contents of all references (including literature references, issued patents, published patent applications, and co-pending patent applications) cited throughout this application are expressly incorporated herein by reference in their entirety. Unless otherwise defined, all technical and scientific terms used herein have the same meaning as commonly known to those skilled in the art. All features disclosed in this specification may be combined in any combination.

Each feature disclosed in this specification may be replaced by alternative features serving the same, equivalent or similar purpose. Thus, unless expressly stated otherwise, each feature disclosed is only an example of a series of equivalent or similar features.

From the above description, one skilled in the art can easily ascertain the essential characteristics of this invention, and can make various changes and modifications of the invention without departing from the spirit and scope of the invention to adapt them to various usages and conditions. Accordingly, other embodiments are within the scope of the appended claims.

What is claimed is:

1. A method of treating a tumor with a KRAS mutation comprising administering to a subject:
   (i) an effective amount of a compound or a pharmaceutically acceptable salt thereof, wherein the compound has a structure of:

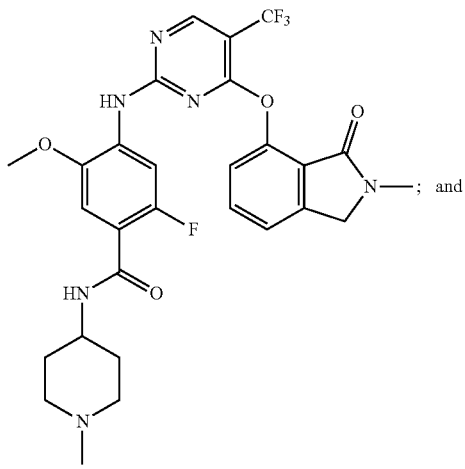

; and (ii) an effective amount of a KRAS inhibitor or an MEK inhibitor.

2. The method of claim 1, wherein the tumor is pancreatic cancer, colorectal cancer, lung cancer, kidney cancer, gastric cancer, prostate cancer or ovarian cancer.

3. The method of claim 1, wherein the KRAS mutation is a G12A, G12C, G12D, G12R, G12S, G12V, G13C, G13D, G13V, Q61K, Q61L, Q61R or Q61H mutation.

4. The method of claim 1, wherein the tumor is 1) lung cancer, colorectal cancer or pancreatic cancer with a KRAS G12C mutation; 2) acute myeloid leukemia with a KRAS G12D, KRAS G12V, KRAS G13D or KRAS Q61H mutation; 3) bladder cancer with a KRAS G12C, KRAS G12D, KRAS G12R, KRAS G12V, KRAS G13D, or KRAS Q61H mutation; 4) breast cancer with a KRAS G12C or KRAS G12V mutation; 5) cervical cancer with a KRAS G12C, KRAS G12D, KRAS G12V, or KRAS G13D mutation; 6) bile duct cancer with a KRAS G12R or KRAS Q61K mutation; 7) colorectal cancer with a KRAS G12A, KRAS G12C, KRAS G12D, or KRAS G13D mutation; 8) esophageal cancer with a KRAS G12D mutation; 9) gastric cancer with a KRAS G12C, KRAS G12D, KRAS G12S, KRAS G12V, KRAS G13D, or KRAS Q61H mutation; 10) glioblastoma with a KRAS G12D mutation; 11) liver cancer with a KRAS G12C, KRAS G12D, or KRAS G13D mutation; 12) lung cancer with a KRAS G12A, KRAS G12D, KRAS G12S, KRAS G12V, KRAS G13C, KRAS G13D, KRAS Q61K, or KRAS Q61L mutation; 13) Melanoma with a KRAS G12C, KRAS G12D, KRAS G12R, KRAS G13D, KRAS Q61K, KRAS Q61L, or KRAS Q61R mutation; 14) mesothelioma with a KRAS G12C mutation; 15) ovarian cancer with a KRAS G12R, KRAS G12V, KRAS Q61L, or KRAS G13C mutation; 16) pancreatic cancer with a KRAS G12A, KRAS G12D, KRAS G12R, KRAS G12V, KRAS G13C, or KRAS Q61H mutation; 17) prostate cancer with a KRAS G12D, KRAS G12R, or KRAS G12V mutation; 18) kidney cancer with a KRAS G12C, KRAS G12D, or KRAS G12V mutation; 19) sarcoma with a KRAS G13C or KRAS Q61H mutation; 20) thyroid cancer with a KRAS G12V, KRAS Q61K, or KRAS Q61R mutation; 21) testicular cancer with a KRAS G12A, KRAS G12R, KRAS G12S, KRAS G12V, KRAS Q61L, or KRAS Q61R mutation; 22) thymoma with a KRAS G12D mutation; or 23) metrocarcinoma with a KRAS G12A, KRAS G12C, KRAS G12D, KRAS G12S, KRAS G12V, KRAS G13C, KRAS G13D, KRAS G13V, KRAS Q61H, or KRAS Q61L mutation.

5. The method of claim 4, wherein the tumor is pancreatic cancer with a KRAS G12C mutation, colorectal cancer with a KRAS G12C mutation, or lung cancer with a KRAS Q61K mutation.

6. The method of claim 5, wherein the tumor is pancreatic cancer with a KRAS G12C mutation.

7. The method of claim 1, wherein the KRAS inhibitor is BI 1701963, JNJ-74699157, MRTX1257, MRTX849, AMG510, or a pharmaceutically acceptable salt thereof, and the AMG510 has a structure of:

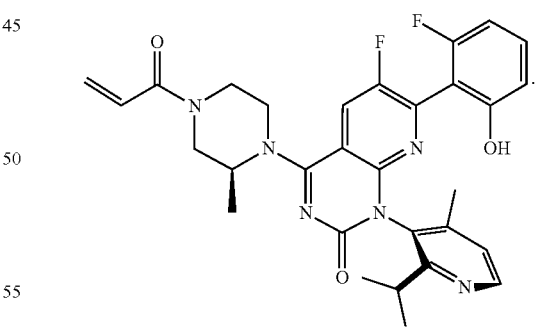

8. The method of claim 7, wherein the KRAS inhibitor is AMG510 or a pharmaceutically acceptable salt thereof.

9. The method of claim 1, wherein the MEK inhibitor is trametinib, cobimetinib, binimetinib, selumetinib, PD-325901, TAK-733, or a pharmaceutically acceptable salt thereof.

10. The method of claim 9, wherein the MEK inhibitor is trametinib or cobimetinib.

11. The method of claim 1, wherein the compound or a pharmaceutically acceptable salt thereof of (i) and the KRAS inhibitor or MEK inhibitor of (ii) are administered simultaneously, alternately or sequentially.

12. The method of claim 1, wherein the pharmaceutically acceptable salt is a tartrate salt.

13. The method of claim 1, further comprising a step of:
a) assessing whether a tissue sample obtained from the subject's cancer has a KRAS mutation before administration.

14. The method of claim 13, further comprising a step of:
b) if the cancer is not characterized by a KRAS mutation, then an anticancer agent other than FAK inhibitors should be administered.

15. The method of claim 1, wherein the KRAS mutation is a G12C, G12D, G13C or Q61K mutation.

* * * * *